(12) United States Patent
Neimark et al.

(10) Patent No.: US 6,731,387 B2
(45) Date of Patent: May 4, 2004

(54) LIGHT BEAM MEASUREMENT OF ABSORPTION BY SUBSTRATES

(76) Inventors: Alexander V. Neimark, 16 Bayberry Dr., Princeton, NJ (US) 08540; Konstantin G. Kornev, 2314 Pleasant Hollow Dr., Plainsboro, NJ (US) 08536; Alexander V. Bazilevsky, Dzerzhinskogo, 2/4 #24, Moscow region, Reutovo (RU), 143964; Aleksey N. Rozhkov, Microrion B, 34, #32, Moscow region, Troitsk (RU), 142191

( * ) Notice: Subject to any disclaimer, the term of this patent is extended or adjusted under 35 U.S.C. 154(b) by 159 days.

(21) Appl. No.: 10/066,688

(22) Filed: Feb. 6, 2002

(65) Prior Publication Data
US 2003/0147079 A1 Aug. 7, 2003

(51) Int. Cl.[7] .............................................. G01N 21/00
(52) U.S. Cl. ...................................... 356/435; 356/440
(58) Field of Search ................................ 356/436, 440; 422/82.05–82.09; 436/164–165, 168

(56) References Cited

U.S. PATENT DOCUMENTS

| | | | |
|---|---|---|---|
| 2,545,281 A | | 3/1951 | Hunt |
| 2,868,062 A | | 1/1959 | Haley |
| 3,591,290 A | * | 7/1971 | Zinner et al. ................ 356/436 |
| 3,635,075 A | | 1/1972 | Gilbert |
| 3,751,167 A | * | 8/1973 | Claus .......................... 356/410 |
| 3,807,875 A | | 4/1974 | Fischer et al. |
| 4,495,149 A | | 1/1985 | Iwata et al. |
| 4,628,468 A | | 12/1986 | Thompson et al. |
| 4,729,659 A | * | 3/1988 | Bessho et al. ............... 356/342 |
| 4,898,462 A | | 2/1990 | Numata et al. |
| 5,239,185 A | | 8/1993 | Ito et al. |
| 6,235,242 B1 | * | 5/2001 | Small et al. .............. 422/82.05 |
| 6,362,890 B1 | * | 3/2002 | Petrich et al. ............... 356/436 |

* cited by examiner

Primary Examiner—Zandra V. Smith
Assistant Examiner—Kara Geisel
(74) Attorney, Agent, or Firm—Clyde I. Coughenour

(57) ABSTRACT

Spontaneous absorption of liquids by porous substrates and capillaries is measured by an optical electronic measuring system providing millisecond resolution of millimeter size droplets. A syringe forms a drop over a porous material or capillary. The absorption time is measured from the instant the lower extreme of the drop formed contacts the porous material or capillary until there is no curvature remaining above the porous material or capillary surface at the location of the drop first contact. The time measurement is also a measurement of the absorption velocity. The absorption velocity characterizes the absorption ability of tested substrates with respect to the testing liquid. The apparatus can be used in microfabrication applications for quantitative analysis of the wettability, permeability, and sorption capacity of structured substrates, including various porous/fibrous materials, chips for microfluidic devices, nano and microelectromechanical systems and chips for protein recognition.

18 Claims, 5 Drawing Sheets

(1)　(2)　(3)

(4)　(5)　(6)

(7)　(8)

LIGHT BEAM MEASUREMENT OF ABSORPTION BY SUBSTRATES

BACKGROUND OF THE INVENTION

1. Field of the Invention

The rate of liquid droplet absorption by a capillary or porous substrate is measured by an optical electronic system.

2. Description of Related Art

Spontaneous penetration of viscous and viscoelastic fluids into pores is observed in various natural and physiological processes and has numerous application in medicine and biomedical engineering, cosmetics and personal care, oil recovery and agriculture, catalysis and separations paper and fiber industries etc. This process may be very fast. Fast absorption is commonly studied by high speed photography. The best commercial instrument known provides up to 350 drop images per second. This is known as the "Drop Shape Analysis System, DSA 10," manufactured by Krüss of Charlotte, N.C.

The use of light beams for measuring and testing are common in the art. S. Hunt, U.S. Pat. No. 2,545,281, issued Mar. 13, 1951, tests liquid absorbency characteristics of materials during successive stages of absorption. The device uses a horizontal surface, a liquid dispenser, a timing device, a light beam and photo cell for determining liquid dispersal. The light beam and timer are used to measure the rate the liquid takes to pass through the dispenser to the material tested. B. Haley, U.S. Pat. No. 2,868,062, issued Jan. 13, 1959, tests absorption using optical means. A roller traverses a ramp and energizes a light source focused on the ramp. Photoelectric means receive light reflected from a liquid treated porous sheet on the ramp while the amount of reflect light with time is kept by a recording means. J. Banner, U.S. Pat. No. 4,720,636, issued Jan. 19, 1988, uses a light beam to detect liquid presence. Phototransistors respond to either the shadow or reflection from the liquid to furnish information to a comparator circuit and an integrator circuit. Thompson et al, U.S. Pat. No. 4,628,468, issued Dec. 9, 1986, teach light beam use for predicting pore-dependent physical properties of microporous solids. The apparatus includes a detector, recording units, a computer and memory. Fischer et al, U.S. Pat. No. 3,807,875, issued Apr. 30, 1974, teach a densitometry apparatus using a light beam passed through a sample to measure chemical concentrations, sedimentation rates, absorption, and light scattering phenomena.

STATE OF THE ART

To better understand the present invention, the art has recognized parameters and characteristics for absorption of materials and knowledge obtained by the expensive and time-consuming photographic procedures incorporated here. These are demonstrated by photographs and graphs. The concepts are inherently applicable to the present invention. To demonstrate these typical viscous and visco-elastic fluids, distilled water, water/glycerin mixture (50/50), aqueous solutions of polyethyleneoxide (PEO) with molecular mass of $4 \times 10^6$, and polyacrylamide (PAM) with molecular mass of $11 \times 10^6$, were used. Stainless steel capillaries of 0.46 mm and 0.65 mm diameters, glass capillaries of 0.65 mm inner diameter, and sugar cubes were used as absorbents.

The surface tension as measured by the drop weight method was 72 nN/m and 65 mN/m for water and for water-glycerin mixture, respectively. In the whole range of studied concentrations, the surface tension of PAM solutions was the same as that of water. The surface tension of PEO solutions depended on the concentration and decreased from 72 mN/m to 62 mN/m as the PEO concentration increased from zero to 100 ppm.

The rheological behavior of the fluids was analyzed by using a co-axial cylinder viscosimeter to measure the shear viscosity and the MicroRheotester developed for testing polymer solutions under stretching. Bazilevsky A. V., Entov V. M., Rozhkov A. N., "Liquid filament microrheometer and some of it's three applications". The Golden Jubilee meeting of the British Society of Rheology and Third European Rheology Conference, 1990, Edinburgh, UK.

The dependencies of the shear viscosity versus the shear rate are presented in FIG. 4. In the process of absorption, the high shear rates are typical. The shear rate can be estimated as $\Gamma \sim U/R$ where U is the velocity of fluid penetration and R is the capillary radius. Taking $U \sim 15$ cm/s and $R = 0.3$ mm we get the estimate of the shear rate as $500\ s^{-1}$. At such large shear rates, $\Gamma \geq 100\ s^{-1}$, the shear viscosity of PEO solutions was practically the same as that of water, 1 mPa·s. At the same time, PAM solutions show a non-Newtonian behavior, especially in the range of shear rates between $100\ s^{-1}$ and $500\ s^{-1}$. As the shear rate increases further, the viscosity of PAM solutions tends to a certain limiting value. For 200 ppm solution, this value is approximated by the viscosity of water, while for 500–1000 ppm solutions, the viscosity of water/glycerin mixture is a suitable estimate.

In MicroRheotester, the dynamics of thinning of liquid filaments is analyzed to characterize the Theological behavior of fluids in extensional flows. It is assumed that the fluid flow can be described by the upper convected Maxwell model. In addition to the shear viscosity inherent in simple liquids, this model involves another physical parameter, the relaxation time $\lambda$. The latter is of the order of a time interval during which the polymer coil assumes its spheroidal shape after deformations. As shown in FIGS. 4 and 5, all polymer solutions showed well pronounced viscoelastic properties.

FIGS. 6–8 show video frames taken during droplet absorption The time intervals between the first, second and third images are about one second. The process takes about 10 ms between the third and fifth images. These images confirm that the droplet remains spherical until it touches the substrate. As soon as the contact is established and the absorption begins, we see the bridge formation preceding instant droplet detachment. Although the time intervals are very small, they are sufficient for stress relaxation. That is why the contact line is held pinned to the capillary brim, and, similarly to the traditional scheme of droplet formation, the detachment is caused by breakdown of the liquid bridge. While the process of bridge rupture is almost unaffected by the substrate properties, there is a striking difference between absorption of water and absorption of polymer solutions. The first four frames in FIGS. 7 and 8 are almost identical and the time intervals between them are comparable. The time intervals between the first, second and third images of FIG. 7 are about one second, between the last four—2–3 milliseconds. In FIG. 8 the time intervals are: between the first, second and third images—2–3 secs, between the third, fourth and fifth—2–3 ms, between the fifth and sixth—14–16 ms, and 0.5 sec between the sixth and the eighth images. The polymer additives do not affect significantly the hydrodynamics of neck formation. They do affect the droplet snap off at the late stages when the neck transforms into a thin filament. Almost cylindrical filaments were detected for water droplets as well, but it disappears swiftly. The stability of the filament formed by a PEO solution reflects the effect inherent with macromolecular solutions: during the bridge thinning the coils are stretched thus forming a bundle of "pins" stabilizing the bridge. The filament lifetime is an order of magnitude longer than the time of neck formation. Thus, the fluid rheology influences the process of droplet detachment significantly. An analysis of the kinetics of filament thinning can be used for the determination of Theological parameters of the fluid.

The dynamics of droplet absorption is quantitatively characterized by FIGS. 3, 9, and 10. A typical record of the optical signals specifying the effect of fluid rheology is presented in FIG. 3. As shown in FIG. 9, the initial droplet size does not influence the process of absorption. Thus the rate of absorption is controlled by pore level effects. The flow rates of water, water/glycerin and 200 ppm PAM solutions differ insignificantly. The average flow rate agrees with the data for water obtained earlier by standard techniques. The kinetics of absorption of polymer solutions is controlled by and is a function of the relaxation time.

In FIG. 10 the mass concentration is specified for each point. As seen from FIGS. 9–10, the velocity reduction is pronounced for the polymer solutions of concentration greater than 200 ppm. The concentration of 200 ppm corresponds to the overlap concentration for PAM solutions when the polymeric coils become occasionally entangled. Above the overlap concentration, the solutions are "jelly;" they manifest the visible effect of normal stresses in shearing flows of viscoelastic fluids.

The above examples show that the method is capable of distinguishing the Theological behavior of tested fluids. The examples reveal a significant difference between absorption of viscous and viscoelastic fluids. It is expected that the method is sensitive enough to catch the characteristic features of absorption of fluids with a more complex Theological behavior, such as biofluids.

SUMMARY OF THE INVENTION

The invention is to a new technique applicable to various substrates. Instead of high speed photography, a millisecond resolution of the change in volume/radius of the droplet remaining atop the substrate is monitored by an optical measuring system.

The optical measuring system consists of a light source, a photo diode with a multiplier connected to a computer through an Analog/Digital converter. A droplet of liquid is emitted from a syringe by a dosing screw. A signal is processed to determine the droplet volume and the time the droplet absorption begins.

Measuring the time interval between the maximum droplet size and disappearance of the droplet we get the time of droplet absorption. A syringe—substrate assembly is placed between a light source and an optical sensor. A droplet is emitted. As soon as it touches the substrate, the fluid begins to penetrate inside the pores. The luminous flux from the light propagating through the gap between the needle of the syringe and the substrate is measured during the process of absorption. An analysis of the dynamics of droplet absorption is reduced to an interpretation of the optical signal. The intensity of the optical signal depends on the cross sectional area of the liquid located in the gap. The intensity of the signal is practically independent of the optical properties of liquids. The signal seen on the screen of the monitor and stored in the computer characterizes the amount of light blocked. Thus, the signal decreases as the droplet penetrates into the substrate. In the simplest version the time interval between the droplet formation and its disappearance due to complete absorption are measured. Since the initial droplet suspended at the syringe is almost spherical, the droplet volume is easily calibrated into the optical signal with a high accuracy. The amount of the absorbed liquid is calculated as the difference between the initial volume and the volume of the residual droplet attached to the syringe. The rate of absorption is quantified by the average volumetric flow rate Q=volume absorbed/time to absorb, or, in the case of capillary, by the average fluid velocity U given by $U=Q/\lambda R^2$, where R is the pore radius.

The method can be used for a wide range of different porous substrates. Among them solid and soft membranes, personal care and biomedical fibrous materials, fibers, rough surfaces, yarns, etc. The technique can also be utilized in the microfabrication applications for quantitative analyses of the wettability, permeability and sorption capacity of structured substrates, including chips for microfluidic devices, nano and micro electromechanical systems, chips for protein recognition, and the like. The method can also be used for screening the effect of the presence, absence, or amount of protein in treated fluids.

DESCRIPTION OF THE PREFERRED EMBODIMENT

Figure 1:
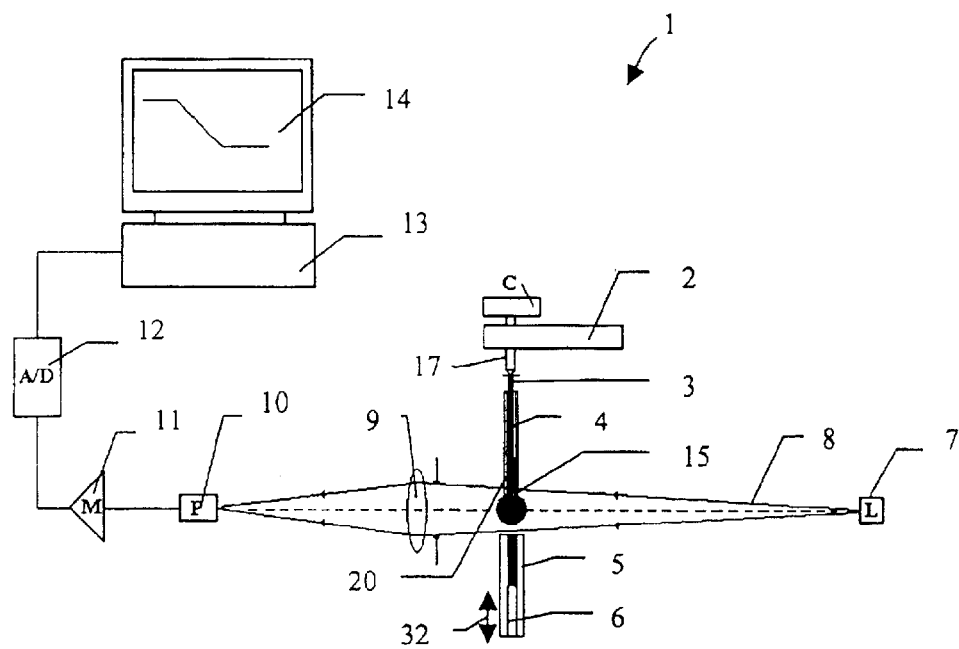
FIG. 1 is a schematic of the testing apparatus arrangement of the invention.

The apparatus 1 for testing the absorption rate of a porous or capillary material is shown in FIG. 1. A dosing control means C activates a dosing screw means 17 to reciprocate a plunger 3 within a syringe 4 to dispense a liquid 20 from the discharge end 15 of the syringe. A porous or capillary material 6 is held on a support 5 below the syringe. The illumination means 7 includes a light source L that casts a light beam 8 between the syringe 4 and support 5. The light that passes through is focused by a lense means 9 into collection means 10 in the form of a photo diode P coupled to a modifier 11, in the form of multiplier M, a converter 12, in the form of an Analog/Digital converter A/D, a computer 13 and monitor 14.

Figure 2:
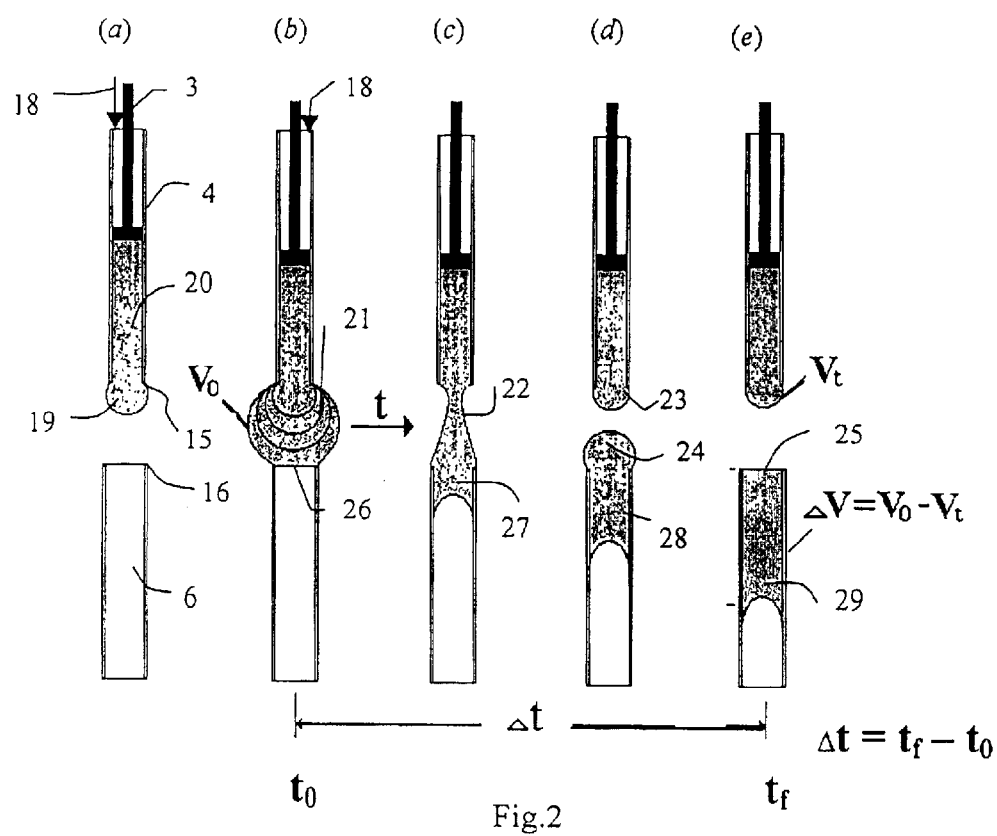
FIGS. 2(a–e) is a schematic representation of a typical absorption sequence over a period of time.
Figure 3:
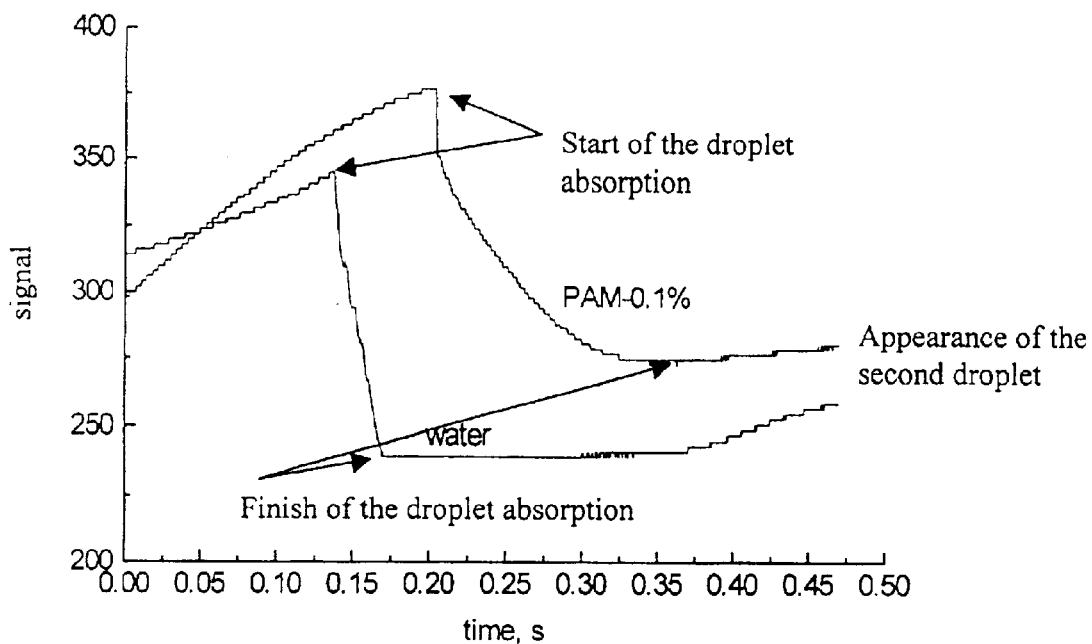
FIG. 3 is a graph of optical signals during the absorption of a water droplet and of a droplet of polyacrylamide solution by a capillary.
Figure 4:
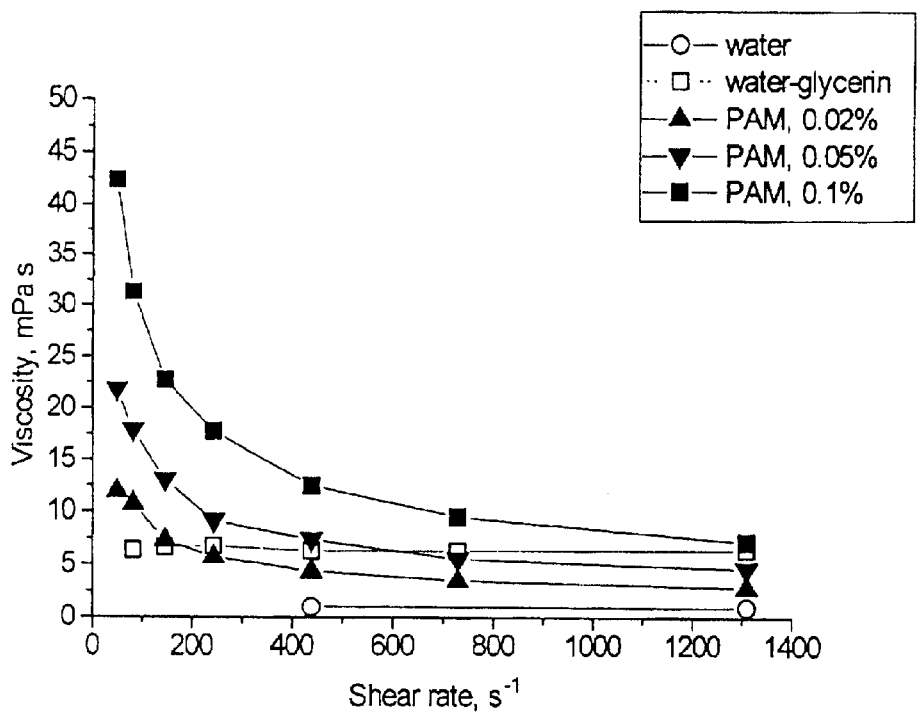
FIG. 4 is a graph of viscosity versus shear rate for different solutions.
Figure 5:
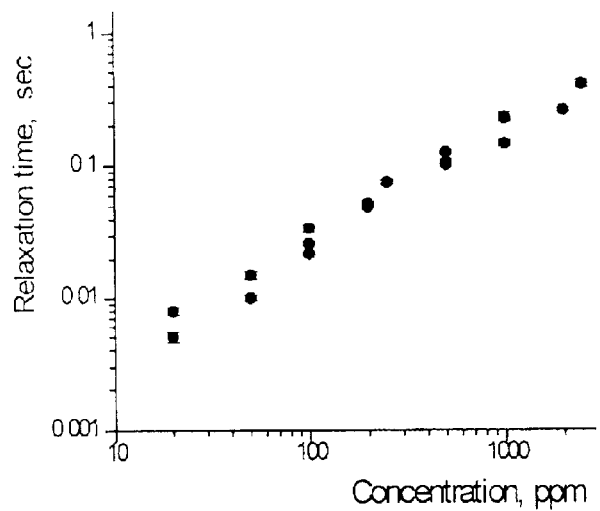
FIG. 5 is a graph of relaxation time as a function of PAM concentration.
Figure 6:
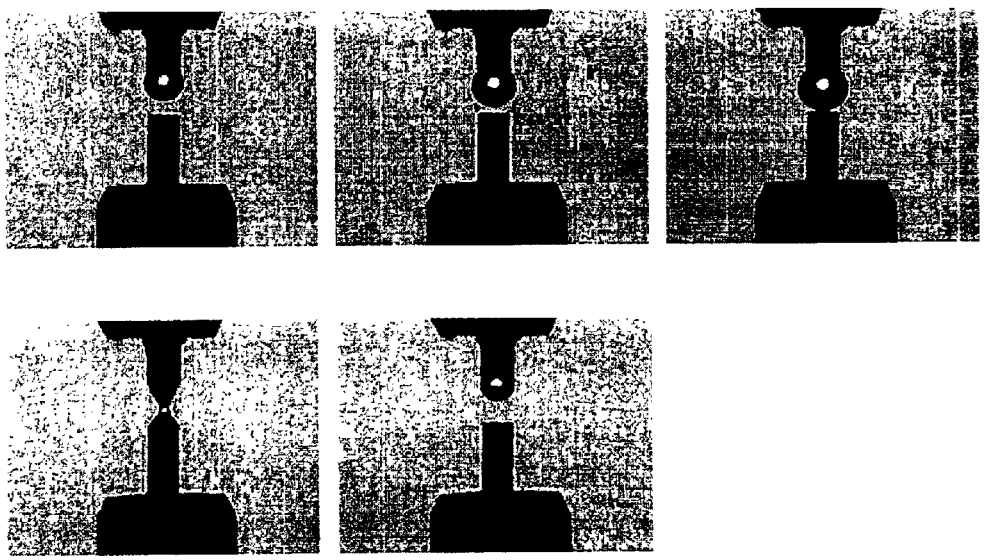
FIG. 6 is video-frames of absorption of a water droplet by a stainless steel capillary.
Figure 7:
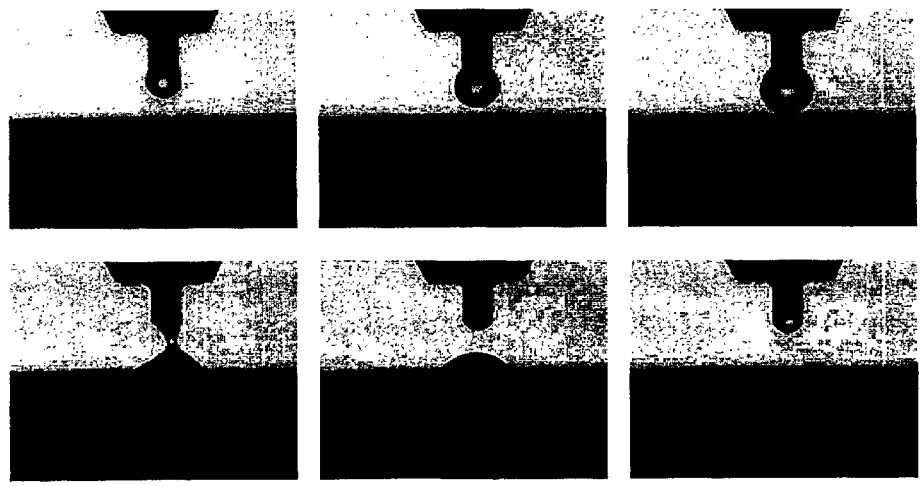
FIG. 7 is video-frames of absorption of a water droplet by a sugar cube.
Figure 8:
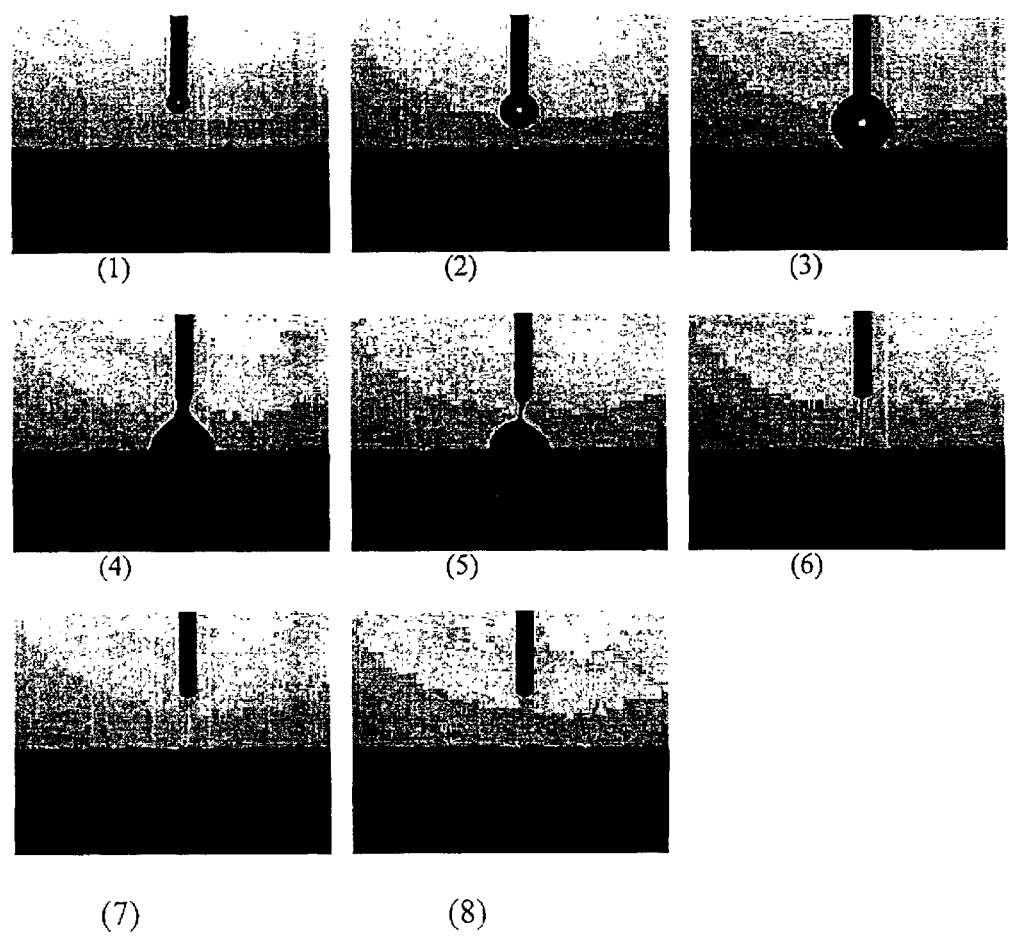
FIG. 8 is video-frames of absorption of a droplet of 100 ppm PEO solution ($\lambda$=0.02 s) by a sugar cube.
Figure 9:
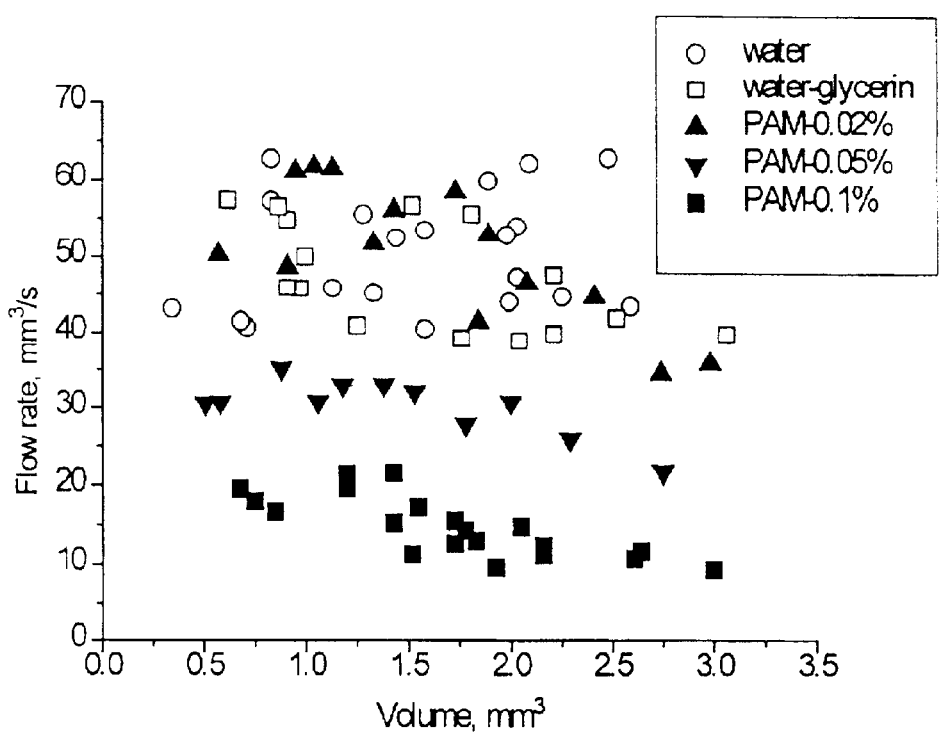
FIG. 9 is a graph of the volumetric rate of intake versus the droplet volume size in glass capillaries.
Figure 10:
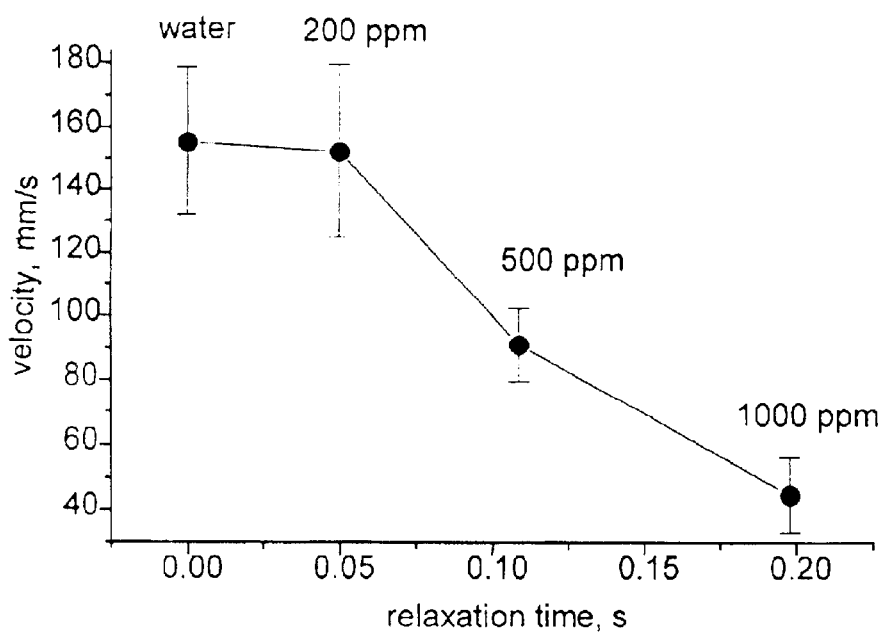
FIG. 10 is a graph of the initial velocity as a function of the relaxation time for PAM in water.

The basic operation of the dosing means and absorption function over time is depicted in FIG. 2, (a–e). In FIG. 2(a) the plunger 3 is lowered 18 within the syringe 4 to form a droplet 19 of liquid 20 on the lower or terminal end 15 of the syringe above a capillary 6 upper end 16. The plunger is lowered until the droplet forms a volume $V_o$ large enough to occupy the space 21 extending between the syringe discharge end 15 and the upper surface 16 of the capillary material 6. The droplet contact 26 with the capillary material upper surface 16, shown in FIG. 2(b), is used to start a time period $t_o$ that is the beginning of absorption by the porous or capillary material. Once contact is made, the downward movement of the plunger is stopped. Once contact is made with the porous material the spherical droplet shape is lost due to the adhesive nature between the liquid and porous material surface characteristics. The absorption 27 of the liquid by the porous material pulls on the liquid tending to remove it from the syringe. This pull results in the formation of a bridge 22 between the porous material and syringe, as shown in FIG. 2(c). As the liquid is further absorbed 28 the liquid bridge is broken down and detached leaving a small residual droplet 23 on the syringe with larger portion of the liquid dropping onto the porous material where it forms intermediate dome 24 over the porous material, as shown in FIG. 2(d). As the liquid is further absorbed, all of the liquid is absorbed into the porous material leaving a flat or non-protruding upper surface 25.

In FIGS. 2, (b) and (e) show the droplet volume $V_o$ that occupies the entire space between the syringe and porous material, and the volume $V_r$, the volume of the residual droplet 23 remaining on the syringe after breaking of the bridge 22. The volume of liquid absorbed 29 by the porous material is the difference between $V_o$ and $V_r$, shown in FIG. 2 as $\Delta V = V_o - V_r$. This absorption into the porous material takes place in the time interval between the instant the liquid droplet contacts with the porous material, FIG. 2(b), and the instant the liquid is absorbed into the porous material, FIG. 2(e). This time interval is shown as $\Delta t$ in FIG. 2.

The method is applicable to test any liquid/substrate pair provided the substrate is wettable by the liquid. The preferred test liquid can be matched to the specific materials used. The preferred test liquids for demonstration purposes are water, water/glycerin mixture, and aqueous solutions of polyethyleneoxide, and polyacrylamide. Any desired material can be tested, and for demonstration purposes various capillaries and sugar cubes are used. The method is applicable to test liquids with unknown properties, such as resulting from mixing, by comparing them to the absorption rate of reference liquids.

The procedure followed is essentially the same for determining the absorption characteristics for a given material having unknown absorption properties. The hydrophilic and/or hydrophobic properties for the material are determined. A liquid is selected either by wanting to know what the material reaction to a specific liquid is, or by the desire to know what the general absorption characteristics of the material are.

Having selected the liquid to be used, the absorption material is placed on the support 5, after which the support is adjusted 32 to be spaced from the liquid dispensing means 4 uniformly Having selected the liquid to be used, the absorption material is placed on the support 5. after which the support is adjusted 32 to be spaced from the liquid dispensing means 4 uniformly or a select distance, taking into consideration the viscosity of the liquid selected.

The light source 7 is activated and the plunger 3, under control of the dosing control means 2, moves down 18 to discharge the liquid 20 from the syringe. A droplet 19 forms and grows in size 21 until it touches 26 the porous material surface 16. Simultaneously with contact between the droplet and the porous material, absorption begins at time $t_o$. The absorption continues during time period $\Delta t$ and lasts until the last part 24 of the liquid is absorbed 25 into the porous material at time $t_f$.

The light beam 8 traveling from the light source 7 to the space between the syringe and porous material is absorbed by or reflected from the liquid 20 at any given time during the absorption process. The light that proceeds past the liquid is focused by lense 9 onto a photo diode 10, then the signal generated in the photo diode is passed through the multiplier 11, where the signal intensity is increased. The stronger signal is then passed on to the converter 12 where the signal is converted from an analog signal into a digital signal that is in turn passed into the computer 13. The digital signals in the computer are compared to previously entered information derived from known flow and absorption characteristics.

Based on these known characteristics for absorption and the specific liquid used, the absorption characteristics for the unknown absorption material such as velocity, volume rate of absorption, etc. can be determined. These findings can be displayed on the monitor 14 for easy visual interpretation.

The invention can be used to study the kinetics of absorption of fluids by porous substrates. As examples, using an optical electronic measuring system with a millisecond resolution, the process of absorption of a single liquid droplet of a given volume is monitored. The time of droplet absorption characterizes the material absorbency. Water solutions of polyethyleneoxide and polyacrylamide were chosen as model viscoelastic fluids. It was shown that the presence of a small amount of polymeric additives causes a significant increase of the time of absorption. The amount of protein in a liquid can be determined by comparison of the pure liquid with known absorption characters of the liquid mixed with various amounts of protein. The wettability, permeability and sorption capacity of structured substrates such as chips for microfluidic devices, nano and microelectromechanical systems, chips for protein recognition and the like can be determined using specific liquid characteristic's information programmed into the computer and comparing it to the absorption ratio recorded by the light collecting means.

It is believed that the construction, operation and advantages of this invention will be apparent to those skilled in the art. It is to be understood that the present disclosure is illustrative only and that changes, variations, substitutions, modifications and equivalents will be readily apparent to one skilled in the art and that such may be made without departing from the spirit of the invention as defined by the following claims.

What is claimed is:

1. An apparatus for measuring absorption comprising:
   a means for dispensing a test liquid;
   a means for supporting an absorption material to be tested a selected distance under said means for dispensing a liquid;
   a light source, for casting a beam of light between said means for dispensing a test liquid and said means for supporting an absorption material, on a first side of said means for supporting an absorption material and means for dispensing a test liquid;
   a light collecting means, for measuring the amount of light that passes through said selected distance between said means for dispensing a test liquid and said means for supporting an absorption material, on a second side;
   a means for measuring the amount of light collected by said light collecting means over a period of time;
   said means for dispensing a test liquid is a syringe;

a plunger under control of a dosing control means dispenses test liquid from said syringe.

2. An apparatus for measuring absorption as in claim 1 including:
said dosing control means initiating test liquid flow and stopping test liquid flow on contact of a formed liquid droplet with an absorption material placed on said means for supporting an absorption material.

3. An apparatus for measuring absorption comprising:
a means for dispensing a test liquid;
a means for supporting an absorption material to be tested a selected distance under said means for dispensing a liquid;
a light source, for casting a beam of light between said means for dispensing a test liquid and said means for supporting an absorption material, on a first side of said means for supporting an absorption material and means for dispensing a test liquid;
a light collecting means, for measuring the amount of light that passes through said selected distance between said means for dispensing a test liquid and said means for supporting an absorption material, on a second side;
a means for measuring the amount of light collected by said light collecting means over a period of time;
a computer for comparing measured light collected data with known absorbed liquid characteristics.

4. An apparatus for measuring absorption as in claim 3 including:
a monitor for displaying the absorption rate of an absorption material being tested as determined by said computer comparison.

5. An apparatus for measuring absorption as in claim 3 wherein:
said light collecting means is a photo diode.

6. An apparatus for measuring absorption as in claim 2 including:
a modifier in the form of a multiplier for increasing the intensity of signals received from said light collecting means;
a computer for comparing absorption data received from a converter of signals received from said modifier with known absorbed liquid characteristics;
a converter in the form of an Analog/Digital converter for convening Analog signals from said light collecting means to digital signals for said computer;
a monitor for displaying the absorption characteristics of the porous material being tested.

7. A process for measuring absorption consisting of:
providing a liquid dispensing means;
providing a light source;
providing a light collecting means;
providing a porous material support;
placing an absorption material on said porous material support;
dispensing a liquid droplet from said dispensing means to said absorption material;
measuring the amount of light that passes between said liquid dispensing means and said porous material support past the dispensed liquid;
measuring the time required for the dispensed liquid droplet to disappear into said absorption material.

8. A process for measuring absorption as in claim 7 including:
measuring the size of the droplet at the instant it contacts said absorption material.

9. A process for measuring absorption as in claim 7 including:
determining the volume of liquid absorbed by said absorption material by comparing the original volume of the liquid droplet to the volume of the original liquid retained on said liquid dispensing means.

10. A process for measuring absorption as in claim 7 including:
focusing the light passing the liquid droplet onto a photo diode light-collecting means using a lens.

11. A process for measuring absorption as in claim 10 including:
multiplying the signal from said photo diode by using a light-collecting signal modifier;
transporting the multiplied signal to an Analog/Digital converter.

12. A process for measuring absorption as in claim 11 including:
transporting the multiplied signal from said Analog/Digital converter to a computer;
analyzing the absorption material's characteristics using said computer;
visually displaying said absorption material's characteristics on a monitor.

13. A process for measuring absorption as in claim 7 including:
providing a computer and evaluating information from said light-collecting means using said computer.

14. A process for measuring absorption as in claim 13 including:
measuring the absorption characteristics of various liquids;
entering the measured absorption characteristics of the various liquids into said computer.

15. A process for measuring absorption as in claim 14 including:
determining the absorption characteristics of said absorption material for the liquid dispensed by comparing the absorption information from said light collecting means with the measured absorption characteristics of the various liquids entered into said computer.

16. A process for measuring absorption as in claim 13 including:
calculating the absorption velocity flow rate of said absorption material using said liquid droplet original volume and said liquid droplet absorption time.

17. A process for measuring absorption as in claim 14 including:
comparing the measured time required for the dispensed liquid droplet to disappear into said absorption material with the measured absorption characteristics of the various liquids entered into said computer;
said absorption material is a structured substrate;
determining the wettability, permeability and sorption capacity of said structured substrate using information programmed into said computer.

18. A process for measuring absorption as in claim 14 including:
determining the amount of protein in a dispensed liquid droplet by comparing the measured time required for the dispensed liquid droplet to disappear into said absorption material with information stored in said computer for the measured time required for a pure liquid droplet to disappear.

* * * * *